US00PP11395P

United States Patent [19]

Holm

[11] Patent Number: Plant 11,395

[45] Date of Patent: May 30, 2000

[54] SPATHOGLOTTIS PLANT NAMED 'LENCARACT'

[75] Inventor: Burkhard Holm, Bedburg-Hau, Germany

[73] Assignee: Tim Lensing-Hebben Pflanzenhandel, Emmerich, Germany

[21] Appl. No.: 09/106,063

[22] Filed: Jun. 29, 1998

[51] Int. Cl.[7] ..... A01H 5/00

[52] U.S. Cl. ..... Plt./311

[58] Field of Search ..... Plt./311, 263

*Primary Examiner*—Howard J. Locker

*Assistant Examiner*—Anne Marie Grünberg

*Attorney, Agent, or Firm*—C. A. Whealy

[57] ABSTRACT

A distinct cultivar of Spathoglottis plant named 'Lencaract' characterized by its relatively compact, upright, and vigorous growth habit; rapid growth rate; elongated leaves that are upright to outwardly arching; numerous large dark purple flowers on strong and erect peduncles; long-lasting flowers; and good postproduction longevity.

1 Drawing Sheet

BACKGROUND OF THE INVENTION

The present invention relates to a new and distinct cultivar of Spathoglottis plant, botanically known as (*Spathoglottis unguiculata* ×*Spathoglottis plicata*), and hereinafter referred to by the cultivar name 'Lencaract'.

The new cultivar is a product of a planned and controlled breeding program conducted by the Inventor in Bedburg-Hau, Germany. The objective of the breeding program is to create new compact Spathoglottis cultivars with large long-lasting flowers, intense flower color, and rapid growth rate.

The new cultivar originated from a cross by the Inventor between an unnamed (*Spathoglottis plicata*) as the female, or seed, parent with an unnamed selection of (*Spathoglottis unguiculata*×*Spathoglottis plicata*) as the male or pollen parent. The cultivar 'Lencaract' was discovered and selected by the Inventor in May, 1995 as a plant within the progeny of the stated cross in a controlled environment in Bedburg-Hau, Germany.

In side-by-side comparisons conducted by the Inventor in Bedburg-Hau, Germany, the following differences between the new Spathoglottis and the female parent, an unnamed selection of *Spathoglottis plicata,* have been observed:

1. Plants of the new Spathoglottis grow faster than plants of the unnamed selection of *Spathoglottis plicata.*

2. Plants of the new Spathoglottis have larger flowers than the unnamed selection of *Spathoglottis plicata.*

3. Flowers of plants of the new Spathoglottis are arranged closer together than flowers of plants of the unnamed selection of *Spathoglottis plicata.*

4. Flower color of plants of the new Spathoglottis is more intense purple than flower color of plants of the unnamed selection of *Spathoglottis plicata.*

5. Leaves of plants of the new Spathoglottis are narrower than leaves of plants of the unnamed selection of *Spathoglottis plicata.*

In side-by-side comparisons conducted by the Inventor in Bedburg-Hau, Germany, the following differences between the new Spathoglottis and the male parent, an unnamed selection of (*Spathoglottis unguiculata*×*Spathoglottis plicata*), have been observed:

1. Plants of the new Spathoglottis have larger flowers than the unnamed selection of (*Spathoglottis unguiculata*× *Spathoglottis plicata).*

2. Inflorescences of plants of the new Spathoglottis are larger than inflorescences of plants of the unnamed selection of (*Spathoglottis unguiculatta*×*Spathoglottis plicata).*

3. Flower color of plants of the new Spathoglottis is darker purple than flower color of plants of the unnamed selection of (*Spathoglottis unguiculatta*×*Spathoglottis plicata).*

4. Leaves of plants of the new Spathoglottis are broader than leaves of plants of the unnamed selection of (*Spathoglottis unguiculata*×*Spathoglottis plicata).*

Asexual propagation by divisions and tissue-culture of the new cultivar at Huissen, The Netherlands, has shown that the unique features of this new Spathoglottis plant are stable and reproduced true to type in successive generations of asexual propagation.

BRIEF SUMMARY OF THE INVENTION

The new Spathoglottis has not been observed under all possible environmental conditions. The phenotype may vary somewhat with variations in environment such as temperature and light intensity, without, however, any variance in genotype.

The following traits have been repeatedly observed and are determined to be the unique characteristics of 'Lencaract'. These characteristics in combination distinguish 'Lencaract' as a new and distinct cultivar:

1. Relatively compact, upright plants.

2. Vigorous growth habit and rapid growth rate.

3. Elongated leaves that are upright to outwardly arching.

4. Numerous large dark purple flowers on strong and erect peduncles.

5. Long-lasting flowers and good post-production longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical potted plant of 'Lencaract'. Flower and leaf colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Bedburg-Hau, Germany, in a glass greenhouse under typical commercial conditions with day and night temperatures averaging 20 and 18° C., respectively, and light levels of about 3,000 lux.

Botanical classification: (*Spathoglottis unguiculata*× *Spathoglottis plicata*) cultivar 'Lencaract'.

Parentage:

*Female parent.*—Unnamed selection of *Spathoglottis plicata.*

*Male parent.*—Unnamed selection of (*Spathoglottis unguiculata*×*Spathoglottis plicata).*

Propagation: By tissue culture.

*Time to initiate roots.*—About 60 days at 20° C.

Plant description:

*Plant shape.*—Upright to outwardly arching elongated leaves and erect flowering stems arising from above-ground pseudobulbs. Appropriate for 13 to 15-cm containers.

*Plant height.*—About 50 cm from soil level to top of leaf plane.

*Plant vigor.*—Vigorous with rapid growth rate.

*Time to finishing.*—About 12 to 15 months are required to produce a flowering finished 14-cm plant from a tissue-cultured plantlet.

*Pseudobulbs.*—Quantity: Usually about five per 13 to 15-cm container. Shape: Ovoid. Length: About 3.5 cm. Width: About 1.5 cm. Color: Medium green with moderate anthocyanin.

*Foliage description.*— Quantity of leaves: About five leaves per pseudobulb, usually about 25 per container. Aspect: Mature leaves held upright to outwardly arching. Length: About 55 cm. Width: About 4 cm. Shape: Elongated, linear; acute apex; entire margin; parallel venation. Texture: Glabrous, plicate. Color: Young and fully expanded, upper surface: 137B/137C. Young and fully expanded, lower surface: 137C/137D.

Flower description:

*Flower arrangement.*—Large purple flowers arranged on a raceme. Peduncles, strong and erect. Typically about six to twelve flowers per flowering stem. Flowering intermittent, usually one inflorescence per pseudobulb at a time. Flowers persistent.

*Natural flowering season.*—April/May until November in the Northern Hemisphere.

*Flower longevity.*—Individual flowers typically last about one week.

*Flower size.*—Length: About 4.5 cm. Width: about 3.5 cm.

*Flower pedicel.*—About 2 cm in length, thin; sparsely pubescent.

*Bracts.*—Appearance/shape: More or less petaloid, strongly concave, broadly elliptic. Color: 78A/80A.

*Petals.*— Length: About 2.25 cm. Width: About 1 cm. Shape: Elliptic. Apex: Acute. Margin: Entire, undulation on lateral petals. Texture: Smooth, satiny. Color: Fully opened, upper and lower surfaces: 80A.

*Slepals.*—Shape: Elliptic. Apex: Acute. Margin: Entire, slight undulation. Texture: Smooth, satiny. Color: 80B/80C.

*Labellum.*— Shape: Tri-lobed. Lateral lobes: Erect; truncate; more or less incurving; 71A/72A. Middle lobe: Stalked; reniform; 71A/72A; claw light yellow at base with some red longitudinal stripes at the base of which with two relatively high comb-shaped extensions with small red dots and long white hairs.

*Column color.*—Dorsal, 71A; ventral, 72A.

*Pollinia.*—Yellow.

*Peduncle.*— Aspect: Strong and erect. Length: About 35 cm. Diameter: Thin, about 6 mm. Texture: Glabrous with some membranous brown sheath leaves. Color: Medium green with medium anthocyanin.

Disease resistance: Under low light conditions, Botrytis may be observed. Resistance to known Spathoglottis diseases has not been observed.

Seed development: Seed development has not been observed.

It is claimed:

1. A new and distinct cultivar of Spathoglottis plant named 'Lencaract', as illustrated and described.

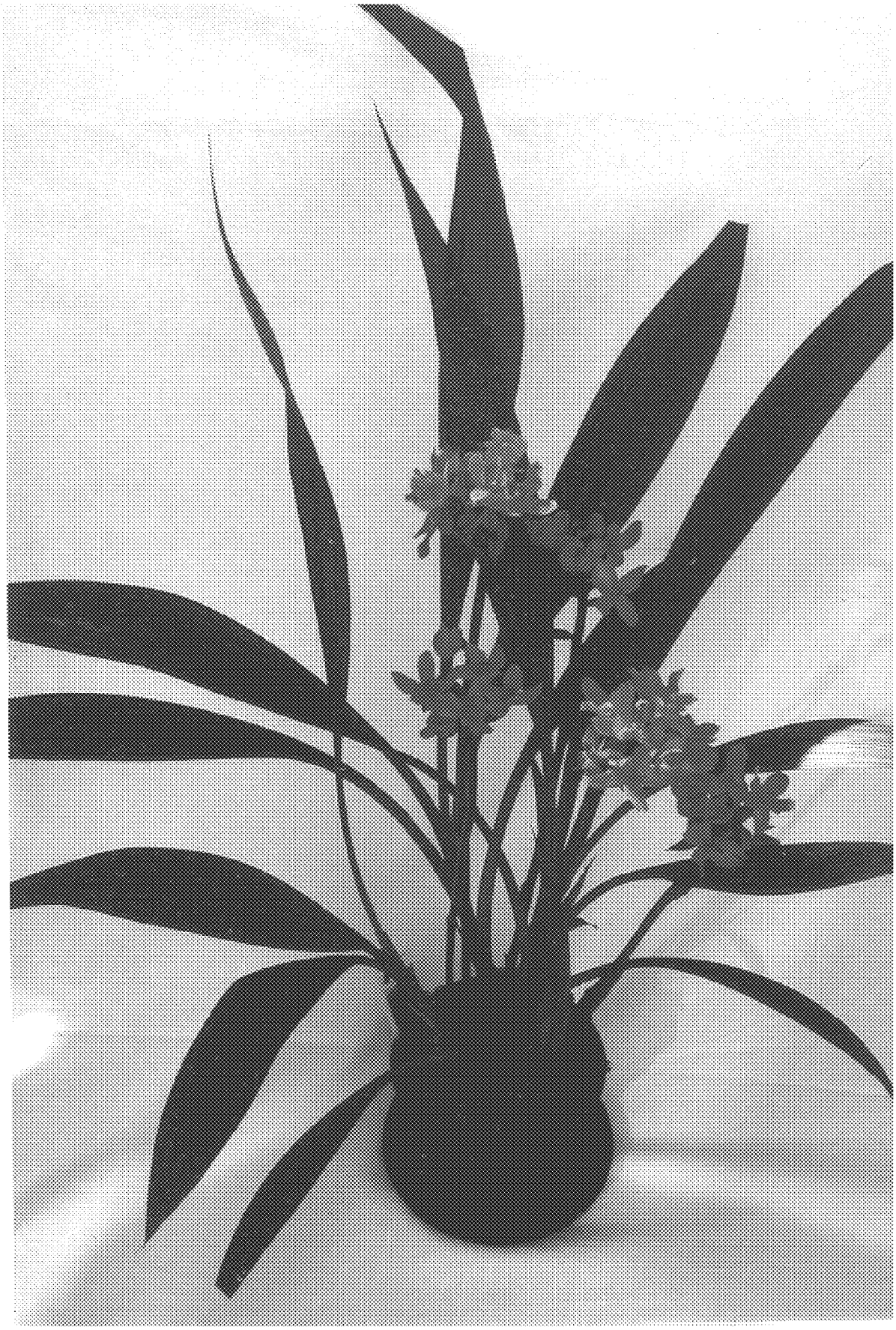

* * * * *